(12) United States Patent
Visintin

(10) Patent No.: US 9,148,045 B2
(45) Date of Patent: Sep. 29, 2015

(54) METHOD AND DEVICE FOR TESTING THE TIGHTNESS OF AN ELECTRIC MACHINE STATOR CORE

(71) Applicant: ALSTOM Technology Ltd, Baden (CH)

(72) Inventor: Massimiliano Visintin, Zürich (CH)

(73) Assignee: ALSTOM TECHNOLOGY LTD., Baden (CH)

( * ) Notice: Subject to any disclaimer, the term of this patent is extended or adjusted under 35 U.S.C. 154(b) by 0 days.

(21) Appl. No.: 13/662,265

(22) Filed: Oct. 26, 2012

(65) Prior Publication Data

US 2013/0047748 A1  Feb. 28, 2013

Related U.S. Application Data

(63) Continuation of application No. PCT/EP2011/056193, filed on Apr. 19, 2011.

(30) Foreign Application Priority Data

Apr. 29, 2010 (EP) ................................ 10161391

(51) Int. Cl.
*G01N 3/00* (2006.01)
*G01M 7/00* (2006.01)
(Continued)

(52) U.S. Cl.
CPC ............... *H02K 15/00* (2013.01); *G01M 7/00* (2013.01); *G01B 7/04* (2013.01); *G01B 7/144* (2013.01); *G01B 7/16* (2013.01); *G01B 17/02* (2013.01); *G01M 7/08* (2013.01); *G01N 29/265* (2013.01); *G01N 2203/0039* (2013.01); *G01N 2203/0617* (2013.01); *G01N 2203/0658* (2013.01); *G01R 31/34* (2013.01); *G01R 31/343* (2013.01); *H02K 15/02* (2013.01); *H02K 2201/03* (2013.01)

(58) Field of Classification Search
CPC .... G01R 31/34; G01R 31/343; G01N 29/265; G01N 2203/0039; G01N 2203/0617; G01N 2203/0658; H02K 15/00; H02K 15/02; G01B 17/02; G01B 7/14; G01B 7/144; G01B 7/16
USPC .......... 73/12.09, 12.12, 865.8; 180/9.21, 9.48
See application file for complete search history.

(56) References Cited

U.S. PATENT DOCUMENTS 3,279,323 A * 10/1966 Asche ................................ 91/20
4,803,563 A * 2/1989 Dailey et al. .................... 348/83
(Continued)

FOREIGN PATENT DOCUMENTS

EP    0403835 B1    8/1994

OTHER PUBLICATIONS

Decision of Grant issued Feb. 9, 2015, by the Russian Patent Office in corresponding Russian Application No. 2012151151, and an English translation thereof.

*Primary Examiner* — Lisa Caputo
*Assistant Examiner* — Jonathan Dunlap
(74) *Attorney, Agent, or Firm* — Buchanan Ingersoll & Rooney PC

(57) ABSTRACT

A method is provided for testing the tightness of an electric machine stator core includes: introducing a test instrument that is connected to a movable support into an air gap between a stator core and a rotor, locally placing the test instrument and locally testing defined zones of the generator stator core. A device for carrying out the method is also provided.

8 Claims, 2 Drawing Sheets

(51) Int. Cl.
*H02K 15/00* (2006.01)
*G01M 7/08* (2006.01)
*G01B 17/02* (2006.01)
*G01B 7/04* (2006.01)
*G01B 7/16* (2006.01)
*G01R 31/34* (2006.01)
*H02K 15/02* (2006.01)
*G01N 29/265* (2006.01)
*G01B 7/14* (2006.01)

(56) References Cited

U.S. PATENT DOCUMENTS

| | | | | |
|---|---|---|---|---|
| 4,887,474 A * | 12/1989 | Sargeant | | 73/865.9 |
| 4,889,000 A * | 12/1989 | Jaafar et al. | | 73/865.8 |
| 4,901,572 A * | 2/1990 | Suyama | | 73/572 |
| 4,962,660 A * | 10/1990 | Dailey et al. | | 73/12.09 |
| 4,970,890 A * | 11/1990 | Jaafar et al. | | 73/12.09 |
| 5,012,684 A * | 5/1991 | Humphries | | 73/865.8 |
| 5,020,234 A * | 6/1991 | Alkire et al. | | 33/656 |
| 5,164,826 A * | 11/1992 | Dailey | | 348/83 |
| 5,295,388 A * | 3/1994 | Fischer et al. | | 73/12.09 |
| 5,365,166 A * | 11/1994 | Dailey et al. | | 324/750.22 |
| 5,473,953 A * | 12/1995 | Appel | | 73/866.5 |
| 5,493,894 A | 2/1996 | Dailey et al. | | |
| 5,557,216 A * | 9/1996 | Dailey et al. | | 324/750.16 |
| 5,563,357 A * | 10/1996 | Longree | | 73/866.5 |
| 5,650,579 A * | 7/1997 | Hatley et al. | | 73/865.8 |
| 6,069,473 A * | 5/2000 | Hatley | | 324/207.18 |
| 6,100,711 A * | 8/2000 | Hatley | | 324/765.01 |
| 6,225,813 B1 | 5/2001 | Garwatoski | | |
| 6,438,861 B1 | 8/2002 | Hatley et al. | | |
| 6,469,504 B1 * | 10/2002 | Kliman et al. | | 324/228 |
| 6,672,413 B2 * | 1/2004 | Moore et al. | | 180/9.21 |
| 6,791,351 B2 * | 9/2004 | Fischer et al. | | 324/765.01 |
| 6,814,169 B2 * | 11/2004 | Moore et al. | | 180/9.21 |
| 6,876,222 B2 * | 4/2005 | Fischer et al. | | 324/765.01 |
| 6,889,783 B1 * | 5/2005 | Moore et al. | | 180/9.21 |
| 6,943,470 B2 * | 9/2005 | Rowe et al. | | 310/58 |
| 7,017,468 B2 * | 3/2006 | Steffen | | 91/41 |
| 7,075,296 B2 * | 7/2006 | Moore | | 324/262 |
| 7,201,055 B1 * | 4/2007 | Bagley et al. | | 73/618 |
| 7,343,828 B2 * | 3/2008 | Bagley et al. | | 73/865.8 |
| 7,418,858 B2 * | 9/2008 | Fischer et al. | | 73/161 |
| 7,520,189 B2 * | 4/2009 | Abbasi et al. | | 73/865.9 |
| 7,555,966 B2 * | 7/2009 | Bagley et al. | | 73/865.8 |
| 7,743,675 B2 * | 6/2010 | Moore | | 73/865.8 |
| 8,220,345 B2 * | 7/2012 | Moser et al. | | 73/866.5 |
| 2004/0148730 A1 * | 8/2004 | Knight et al. | | 15/339 |
| 2005/0116555 A1 * | 6/2005 | Rowe et al. | | 310/58 |
| 2007/0089544 A1 * | 4/2007 | Bagley et al. | | 73/865.8 |
| 2007/0277629 A1 * | 12/2007 | Bagley et al. | | 73/865.8 |
| 2007/0277630 A1 * | 12/2007 | Bagley et al. | | 73/865.9 |
| 2008/0087112 A1 * | 4/2008 | Bagley et al. | | 73/865.8 |
| 2008/0087113 A1 * | 4/2008 | Bagley et al. | | 73/865.8 |
| 2008/0098832 A1 * | 5/2008 | Abbasi et al. | | 73/865.9 |
| 2009/0301168 A1 | 12/2009 | Moore | | |

* cited by examiner

METHOD AND DEVICE FOR TESTING THE TIGHTNESS OF AN ELECTRIC MACHINE STATOR CORE

INCORPORATION BY REFERENCE

The following documents are incorporated herein by reference as if fully set forth: International Patent Application No. PCT/EP2011/056193, filed Apr. 19, 2011—and—European Patent Application No. 10161391.7, filed Apr. 29, 2010.

TECHNICAL FIELD

The present invention relates to method and a device for testing the tightness of an electric machine stator core.

BACKGROUND OF THE INVENTION

Electric machines are generally known to comprise an annular stator and an internal rotor, however different topologies have been already adopted and are actually manufactured.

The stator comprises an iron core provided with slots housing the stator winding. The stator core is made of packets of electrically insulated iron sheets, joined together by thin spacers, which define the cooling channels between the packets for the relevant cooling gas flow.

All stator packets and the spacers are tightened together under pressure by means of press plates at both core ends and additional key bars, generally welded to the core back and to both press plates.

During operation, the stator core can loose its tightness, due to electromagnetic, mechanical and thermal stresses and aging. In particular the iron sheets can start to separate from each other and to vibrate, finally leading to localized hot spots due to short circuits of the sheets and/or to breakdown in the stator winding, i.e. to electric machine failures.

In addition, in case an upgrade (to increase its rated power) or a rewind of the electric machine is foreseen, the stator core conditions must be checked to assess whether it is capable of withstanding the new operating conditions or respectively bearing the expected lifetime extension. The tightness of the stator core is one of the required assessments of the electric machine conditions, which are to be performed before any renewal.

Traditionally, in order to test the stator core tightness, the rotor must be extracted so as to allow enough space within the stator to perform the required tests.

However, rotor extraction is very time consuming and both rewinds and upgrades have strict time constraints for the full implementation. In addition, rotor extraction creates a risk of stator and/or rotor damage.

SUMMARY OF THE INVENTION

The present disclosure is directed to a method for testing the tightness of an electric machine stator core. The electric machine has a stator core and a rotor defining an air gap therebetween. The method includes introducing a test instrument that is connected to a movable support into the air gap, locally placing the test instrument and locally testing defined zones of the generator stator core.

The present disclosure is also directed to a device for testing the tightness of an electric machine stator core, including a movable support, insertable in an air gap between an electric generator stator core and a rotor. The device also includes a test instrument carried by the movable support and locally positionable to locally test defined zones of the generator stator core.

BRIEF DESCRIPTION OF THE DRAWINGS

Further characteristics and advantages of the invention will be more clear from the description of a preferred but non-exclusive embodiment of the method and device, illustrated by way of non-limiting example in the accompanying drawings, in which.

DETAILED DESCRIPTION OF EMBODIMENTS OF THE INVENTION

Introduction to the Embodiments

Figure 1:
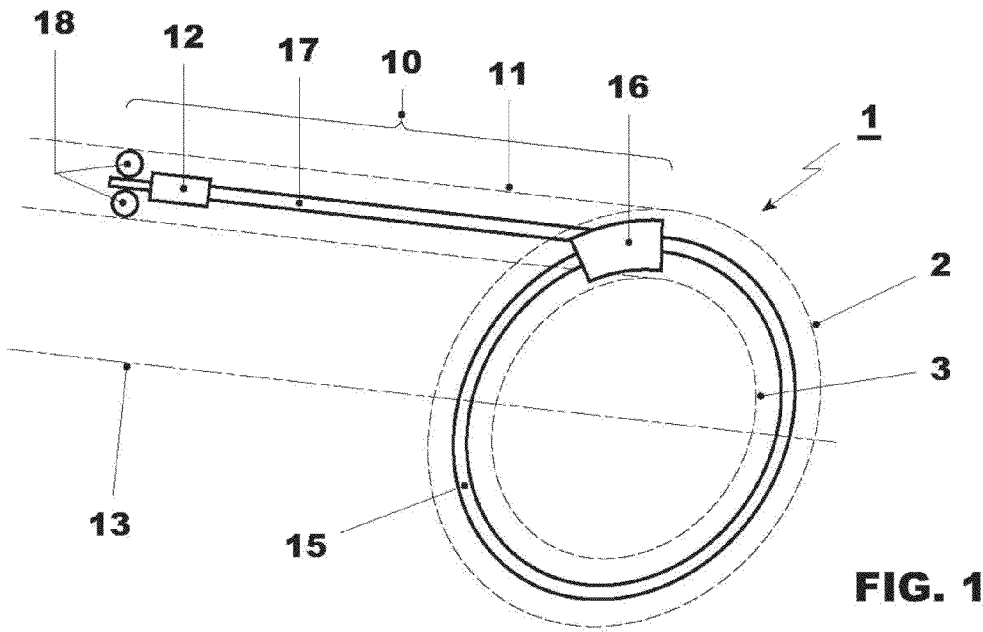
FIG. 1 is a schematic view of a device associated to a stator core and rotor (in dashed lines) of an electric machine such as an electric generator.

The technical aim of the present invention is therefore to provide a method and a device by which the said problems of the known art are eliminated.

Within the scope of this technical aim, an aspect of the invention is to provide a method and a device that permit tests for ascertaining the tightness of the stator core to be carried out without the need of rotor extraction.

Another aspect of the invention is to provide a method and a device that allow tests to be carried out in an easy and fast manner.

A further aspect of the invention is to provide a method and a device that reduce the risks that the stator core and/or the rotor are damaged because of the tightness tests.

The technical aim, together with these and further aspects, are attained according to the invention by providing a method and a device in accordance with the accompanying claims.

DETAILED DESCRIPTION

With reference to the figures, reference number 1 generally indicates an electric machine such as an electric generator having a stator core 2 and a rotor 3.

The stator core 2 is made of a plurality of packets 4 of iron sheets 5 that are spaced apart by means of ventilation spacers (such as ribs, not shown) to determine the stator core cooling channels 6.

The device for testing the tightness of the stator core 2 comprises a movable support 10, which can be introduced into the air gap 11 between the stator core 2 and the rotor 3.

The support 10 carries a test instrument 12 to locally place it within the gap 11 and locally test defined zones of the generator stator core 2.

Preferably, the support 10 is arranged to place the test instruments 12 over at least half of the air gap axial length (i.e. the length of the air gap 11 along the longitudinal axis 13 of the electric machine such as generator).

In particular, the support 10 may be able to place the test instrument 12 over the whole air gap axial length, such that it is possible to test the whole stator core 2 by mounting the device 1 only once, or over half the gap axial length, such that it is possible to test the whole stator core by mounting the device 1 twice (i.e. at both stator core ends).

The support 10 comprises a guide 15 that can be circumferentially connected to the electric machine such as generator 1 along the air gap 11 (for example it can be connected to the retaining ring of the generator); preferably the guide 15 extends over the whole air gap circumferential length, such that the whole stator core 2 may be tested by mounting the device 1 only once, it is anyhow possible that in different embodiments the guide 15 circumferentially extends over only a part of the air gap 11.

The guide 15 carries a cart 16, movable along it to reach different circumferential positions of the stator core 2.

The cart 16 carries an extendable arm 17 that carries the test instrument 12.

In addition, the extendable arm may be provided with wheels 18 to guarantee a secure connection to the stator core 2 and/or rotor 3 during test operations.

In the following, particular embodiments of the invention with different test instruments are described.

Figure 2:
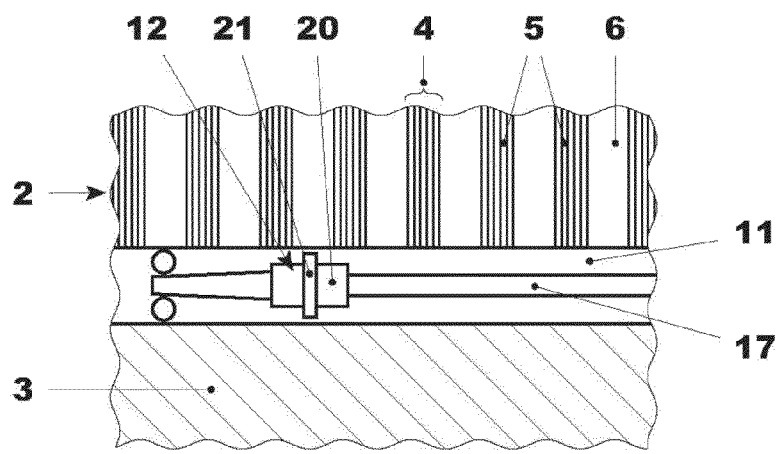
FIGS. 2 and 3 show a particular of a first embodiment of the invention.
Figure 3:
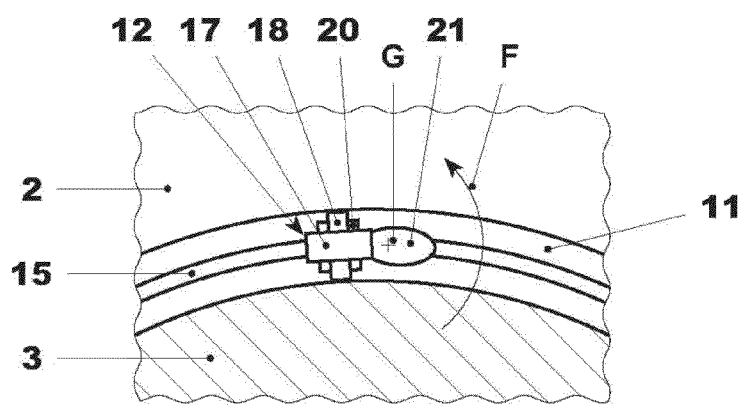

FIGS. 2 and 3 show an embodiment in which the test instrument 12 comprises a mechanical sensor.

As shown in FIGS. 2 and 3, the arm 17 has a detecting head 20 that has hinged a mechanical sensor such as an elliptical plate 21 that can rotate, around an axis G, between an inserting position (as shown in FIGS. 2 and 3) and a testing position, rotated as indicated by arrow F.

Testing with this mechanical sensor is achieved by placing the plate 21 in the zone of the stator core 2 to be tested, and then making the plate 21 rotate as indicated by the arrow F; the force to be applied to the plate 21 to make it enter into a packet 4 between the iron sheets 5 is proportional to the remaining stiffness of the packet 4 to be measured.

Figure 4:
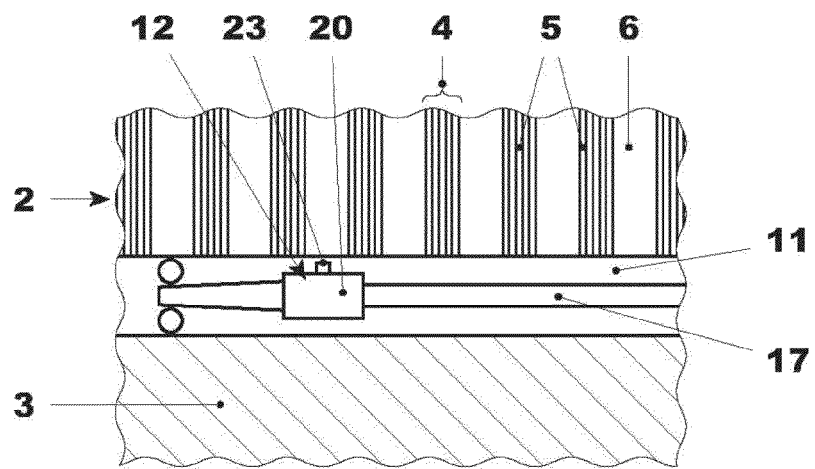
FIGS. 4 through 6 show further embodiments of the invention.
Figure 5:
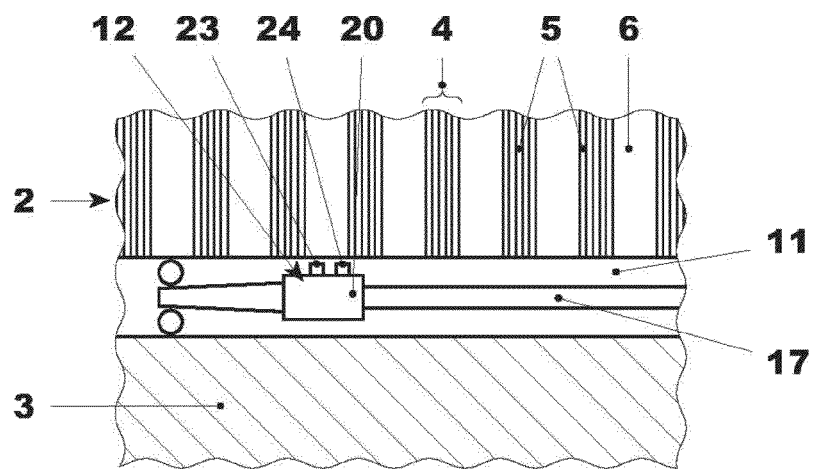

FIGS. 4 and 5 show two different embodiments in which the testing instrument comprises an electric sensor.

In these embodiments a detecting head 20 connected to the arm 17 carries a sensor such as a coil 23 arranged to inject a high frequency magnetic flux into a packet 4, so as to induce a proper vibration of it.

A signal generated by the vibrating packet may be detected using the same coil 23 (as shown in FIG. 4), or using a different sensor 24 (as shown in FIG. 5).

In particular, the sensor 24 may be an electric sensor, such as a second coil, or an acoustic sensor, such as a microphone, or a mechanical sensor, such as an accelerometer to be placed onto the packet 4 under testing (for example in this case the sensor 24 may be supported by an auxiliary arm movable towards the stator core and vice versa).

Alternatively, the sensor 23 may be an acoustic sensor that generates an acoustic signal that makes the packet 4 vibrate and also detects the signal generated by the vibrating packet.

In addition, in this case a second sensor 24 may also be provided and, as already described; it may be an electric sensor such as a coil, an acoustic sensor such as a microphone or a mechanical sensor such as an accelerometer to be placed on the packet 4 to be tested.

Figure 6:
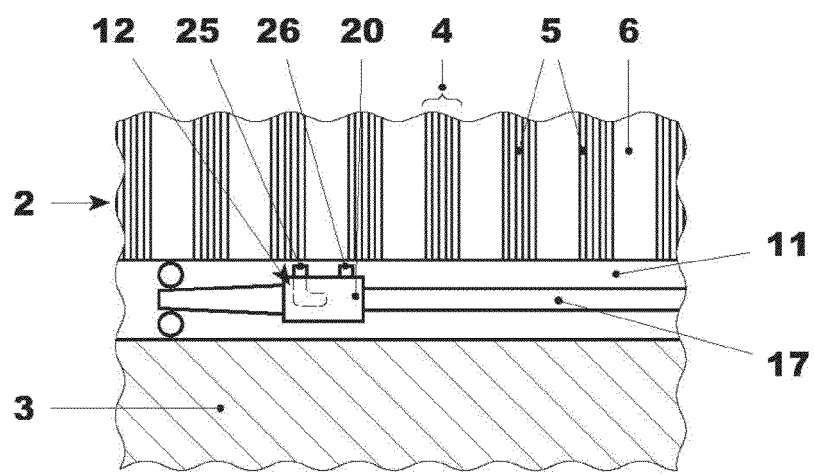

FIG. 6 represents another embodiment, wherein the test instrument 12 comprises a mechanical sensor.

In this embodiment a detecting head 20 connected to the arm 17 carries an electric driven mechanical device such as a hammer 25 (micro-hammer), which hits the packet 4 so as to make it vibrate. The signal generated by the vibrating packet can be detected by another sensor 26. In particular the sensor 26 may be a mechanical sensor such as an accelerometer or an acoustic sensor such as a microphone.

Combination of the embodiments shown in FIGS. 2 through 6 is also possible.

The method for testing the tightness of an electric machine stator core with the rotor 3 inserted in the stator core 2 comprises:

introducing the test instrument 12 that is connected to a movable support 10 into the air gap 11 between the stator core 2 and the rotor 3, locally placing the test instrument 12, i.e. placing the test instrument 12 in correspondence of the zone of the stator core 2 to be tested. This can be done by regulating the axial and circumferential position of the test instrument 12 within the gap 11;

locally testing defined zones of the generator stator core 2.

Since testing is carried out on defined zones of the stator core 2 and since the testing instrument 12 may be brought in correspondence of any zone of the stator core 2, it is possible to test only the packets 4 that are more subject to become loose.

In addition, since tests are carried out locally, the exact position of the loose packets 4 is automatically known (because it is known the axial and the circumferential position where the tests are carried out).

Advantageously, tests are repeated a number of times at different axial and/or angular positions.

In different embodiments, tests are carried out by introducing the plate 21 between the stator core iron sheets 5, or by stressing the stator core iron sheets 5 to make them vibrate and detecting the vibrations. Preferably vibrations are detected by measuring a signal generated by the vibrating iron sheets 5.

Naturally the features described may be independently provided from one another.

In practice the materials used and the dimensions can be chosen at will according to requirements and to the state of the art.

It is understood, therefore, that this invention is not limited to the particular embodiments disclosed, but is intended to cover all modifications which are within the spirit and scope of the invention as defined by the appended claims; the above description; and/or shown in the attached drawings.

REFERENCE NUMBERS

1 electric machine (electric generator)
2 stator core
3 rotor
4 packets of 5
5 iron sheets
6 cooling channels
10 support
11 air gap
12 test instrument
13 longitudinal axis of 1
15 guide
16 cart
17 extendable arm
18 wheels
20 detecting head
21 plate
23 sensor
24 sensor
25 micro-hammer
26 sensor
F arrow
G rotation axis

What is claimed is:

1. Method for testing the tightness of an electric machine stator core, wherein the electric machine comprises a stator core formed of iron sheets and a rotor defining an air gap therebetween, the method comprising:

introducing a test instrument connected to a support into the air gap, the test instrument including a plate, the support including a guide circumferentially connected to an outer face of the rotor core of the electric machine, and fixed in a longitudinal axial direction of the rotor core, and a cart being movable along the guide to reach circumferential positions of the stator core, the cart including a longitudinally extendable arm projecting along the longitudinal axis of the rotor core perpendicular to the guide, the test instrument being arranged on a terminal end of the arm distal to the cart;

locally placing the test instrument in a zone of the stator core; and locally testing defined zones of the stator core by rotating the plate arranged on the arm about an axis defined within the plate between an insertion position and a testing position, from which the plate is introduced between the stator core iron sheets.

2. The method as claimed in claim 1, wherein tests are repeated a number of times at different axial and/or angular positions.

3. The method as claimed in claim 1, wherein the plate is elliptical.

4. Device, for testing the tightness of a stator core, formed of iron sheets, of an electric machine, comprising:

a support, insertable in an air gap between an electric generator stator core and a rotor, the support including a guide circumferentially connected to an outer face of the rotor core of the electric machine, and fixed in a longitudinal axial direction of the rotor core and a cart movable along the guide to reach circumferential positions of the stator core;

a test instrument carried by the cart, the test instrument being locally positionable to locally test defined zones of the generator stator core wherein the cart is connected to a longitudinally extendable arm that carries the test instrument, the arm projecting along the longitudinal axis of the rotor core perpendicular to the guide and the test instrument being arranged on a terminal end of the arm distal to the cart; and a plate arranged on the arm and configured to be rotatable about an axis defined within the plate, between an insertion position and a testing position, the plate configured to be introduced between the stator core iron sheets.

5. The device as claimed in claim 4, wherein said support is arranged to place the test instrument over at least half of an axial length of the gap.

6. The device as claimed in claim 4, wherein the plate is elliptical.

7. Method for testing the tightness of an electric machine stator core, wherein the electric machine comprises a stator core formed of iron sheets and a rotor defining an air gap therebetween, the method comprising:

introducing a test instrument connected to a support into the air gap, the test instrument including a plate, the support including a guide circumferentially connected to an outer face of the rotor core of the electric machine, and fixed in a longitudinal axial direction of the rotor core, and a cart being movable along the guide, the cart including an arm projecting along the longitudinal axis of the rotor core perpendicular to the frame, the test instrument being arranged on a terminal end of the arm distal to the cart;

locally placing the test instrument in a zone of the stator core; and locally testing defined zones of the stator core by rotating the plate arranged on the arm about an axis defined within the plate between an insertion position and a testing position, from which the plate is introduced between the stator core iron sheets.

8. The method as claimed in claim 7, wherein the plate is elliptical.

* * * * *